US011400138B2

(12) United States Patent
Lin et al.

(10) Patent No.: US 11,400,138 B2
(45) Date of Patent: Aug. 2, 2022

(54) METHOD FOR IMPROVING SKIN CONDITION WITH BIOACTIVE COMPOUND

(71) Applicant: TCI CO., LTD., Taipei (TW)

(72) Inventors: Yung-Hsiang Lin, Taipei (TW); Yu-Ling Wang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/099,784

(22) Filed: Nov. 17, 2020

(65) Prior Publication Data

US 2022/0040268 A1 Feb. 10, 2022

(30) Foreign Application Priority Data

Aug. 6, 2020 (TW) ................ 109126750

(51) Int. Cl.
| | | |
|---|---|---|
| *A61K 38/39* | (2006.01) | |
| *A61K 8/65* | (2006.01) | |
| *A61P 17/00* | (2006.01) | |
| *A61P 17/02* | (2006.01) | |
| *A61P 17/04* | (2006.01) | |
| *A61P 17/06* | (2006.01) | |
| *A61P 17/08* | (2006.01) | |
| *A61P 17/10* | (2006.01) | |
| *A61P 17/12* | (2006.01) | |
| *A61P 17/14* | (2006.01) | |
| *A61K 38/17* | (2006.01) | |

(52) U.S. Cl.
CPC ............... *A61K 38/39* (2013.01); *A61K 8/65* (2013.01); *A61K 38/1706* (2013.01)

(58) Field of Classification Search
CPC .... A61K 38/39; A61K 8/65; A61K 38/17905; A61P 17/00; A61P 17/02; A61P 17/04; A61P 17/06; A61P 17/08; A61P 17/10; A61P 17/12; A61P 17/14
See application file for complete search history.

(56) References Cited

U.S. PATENT DOCUMENTS

| | | | | |
|---|---|---|---|---|
| 7,745,391 B2* | 6/2010 | Mintz | ................ | A61P 37/00 |
| | | | | 514/19.3 |
| 9,238,822 B2* | 1/2016 | Baum | ............... | C12N 15/8279 |
| 10,155,804 B2* | 12/2018 | Morimoto | .............. | A61K 38/17 |
| 10,435,457 B2* | 10/2019 | Watters | ................. | C07K 14/78 |
| 10,463,711 B2* | 11/2019 | Hamill | .................. | A61K 38/10 |
| 2003/0233675 A1* | 12/2003 | Cao | .................... | C12N 15/8251 |
| | | | | 536/23.6 |
| 2007/0189981 A1* | 8/2007 | Ross | ....................... | A61K 8/64 |
| | | | | 435/69.3 |
| 2013/0259924 A1* | 10/2013 | Bancel | ..................... | A61P 7/00 |
| | | | | 530/358 |

OTHER PUBLICATIONS

Skin Conditions from Merck Manual, pp. 1-3. Accessed Feb. 6, 2022. (Year: 2022).*
Alphabetical list of Skin Diseases from skinsight.com, pp. 1-60. Accessed Feb. 6, 2022. (Year: 2022).*
Alopecia from Merck Manual, pp. 1-9. Accessed Nov. 2, 2020. (Year: 2020).*
Alopecia Areata from Merck Manual, pp. 1-3. Accessed Nov. 2, 2020. (Year: 2020).*
Marine Fish Proteins and Peptides for Cosmeceuticals: A Review., Venkatesan et al., Marine Drugs, vol. 15, Issue 143, May 18, 2017, 18 pages Full text, pp. 5-6, 8-10.
Effects of fish collagen peptides on collagen post-translational modifications and mineralization in an osteoblastic cell culture system., Yamada et al., Dental Material Journal, vol. 32, Issue 1, Sep. 23, 2013, pp. 88-95 p. 4, Gene expression of type I collagen, LH isoforms, LOX, LOXL isoforms and GLT25D1.
Oral Intake of Collagen Peptide Attenuates Ultraviolet B Irradiation-Induced Skin Dehydration In Vivo by Regulating Hyaluronic Acid Synthesis., Kang et al., International Journalof Molecular Science, vol. 19, Issue 11, Nov. 11, 2018, 12 pages p. 3, Hyaluronic Acid Production and HAS and HYAL mRNA and Protein Expression in the Skin Tissue of UV-Irradiated Hairless Mice Treated with Collagen Peptide.

\* cited by examiner

*Primary Examiner* — Julie Ha
(74) *Attorney, Agent, or Firm* — Chieh-Mei Wang

(57) ABSTRACT

A method for improving a skin condition of a subject in need thereof includes administering to the subject a composition including a bioactive compound. The bioactive compound is a peptide, and includes at least one amino acid sequence as set forth in SEQ ID NO: 1 to SEQ ID NO: 11. Each of the amino acid sequence is a peptide of fish skin.

7 Claims, 11 Drawing Sheets

Specification includes a Sequence Listing.

SEQUENCE LISTING

<160> NUMBER OF SEQ ID NOS: 25

<210> SEQ ID NO 1
<211> LENGTH: 7
<212> TYPE: PRT
<213> ORGANISM: Oreochromis mossambicus

```
<400> SEQUENCE: 1

Gly Phe Asp Ile Gly Phe Ile
1               5

<210> SEQ ID NO 2
<211> LENGTH: 9
<212> TYPE: PRT
<213> ORGANISM: Oreochromis mossambicus

<400> SEQUENCE: 2

Gly Leu Pro Gly Val Gln Gly Asn Ile
1               5

<210> SEQ ID NO 3
<211> LENGTH: 12
<212> TYPE: PRT
<213> ORGANISM: Oreochromis mossambicus

<400> SEQUENCE: 3

Ile Gly Ile Phe Gly Gln Thr Gly Pro Pro Gly Glu
1               5                   10

<210> SEQ ID NO 4
<211> LENGTH: 12
<212> TYPE: PRT
<213> ORGANISM: Oreochromis mossambicus

<400> SEQUENCE: 4

Pro Gly Pro Met Gly Pro Met Gly Ile Asn Gly Ala
1               5                   10

<210> SEQ ID NO 5
<211> LENGTH: 20
<212> TYPE: PRT
<213> ORGANISM: Oreochromis mossambicus

<400> SEQUENCE: 5

Ala Val Asn Gly Leu Thr Leu Ala Gly Gly Arg Gly Leu Asn Thr Gly
1               5                   10                  15

Ala Ala Leu Thr
            20

<210> SEQ ID NO 6
<211> LENGTH: 9
<212> TYPE: PRT
<213> ORGANISM: Oreochromis mossambicus

<400> SEQUENCE: 6

Ala Leu Val Gln Asn Arg Glu Gly Pro
1               5

<210> SEQ ID NO 7
<211> LENGTH: 15
<212> TYPE: PRT
<213> ORGANISM: Oreochromis mossambicus

<400> SEQUENCE: 7

Asn Gly Leu Pro Gly Ser Pro Gly Leu Pro Gly Arg Gln Gly Glu
1               5                   10                  15

<210> SEQ ID NO 8
<211> LENGTH: 21
<212> TYPE: PRT
```

```
<213> ORGANISM: Oreochromis mossambicus

<400> SEQUENCE: 8

Pro Gly Gln Pro Gly Leu Ser Gly Val Pro Gly Ala Asp Gly Lys Pro
1               5                   10                  15

Gly Leu Pro Gly Pro
            20

<210> SEQ ID NO 9
<211> LENGTH: 7
<212> TYPE: PRT
<213> ORGANISM: Oreochromis mossambicus

<400> SEQUENCE: 9

Met Phe Gly Lys Asp Val Trp
1               5

<210> SEQ ID NO 10
<211> LENGTH: 7
<212> TYPE: PRT
<213> ORGANISM: Oreochromis mossambicus

<400> SEQUENCE: 10

Asp Gln Gly Ile Arg Leu Leu
1               5

<210> SEQ ID NO 11
<211> LENGTH: 11
<212> TYPE: PRT
<213> ORGANISM: Oreochromis mossambicus

<400> SEQUENCE: 11

Gln Arg Gly Glu Pro Gly Pro Asn Gly Ala Val
1               5                   10

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tttagcgtcc tacacgagcc                                               20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
ccatccaggg caacagtaag c                                             21

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
cggcggagga aaactgtct                                                19
```

```
<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
tcggctgggt aagaaatctg a                                              21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
agagtgtctg cggatacttc c                                              21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
ccaacagtgt aggtcttggt g                                              21

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18 gataccccctt tgacggtaag ga                                            22

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
ccttctccca aggtccatag c                                              21

<210> SEQ ID NO 20
<211> LENGTH: 20
<212> TYPE: DNA
<213> ORGANISM: Artificial Sequence
<220> FEATURE:
<223> OTHER INFORMATION: Artificial Sequence

<400> SEQUENCE: 20
ctgggtgctg tgtgttttga                                                20

<210> SEQ ID NO 21
<211> LENGTH: 20
<212> TYPE: DNA
<213> ORGANISM: Artificial Sequence
<220> FEATURE:
<223> OTHER INFORMATION: 1
```

```
<400> SEQUENCE: 21
tgagtcttgt tttgccctgc                                              20

<210> SEQ ID NO 22
<211> LENGTH: 20
<212> TYPE: DNA
<213> ORGANISM: Artificial Sequence
<220> FEATURE:
<223> OTHER INFORMATION: Artificial Sequence

<400> SEQUENCE: 22
cggtgctcca aaaggcaaa                                               20

<210> SEQ ID NO 23
<211> LENGTH: 20
<212> TYPE: DNA
<213> ORGANISM: Artificial Sequence
<220> FEATURE:
<223> OTHER INFORMATION: Artificial Sequence

<400> SEQUENCE: 23
acacaatgag ttgggcgaga                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
gctaaggcag ccaagtatgg                                              20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cacctgggac aactggaatc                                              20
```

METHOD FOR IMPROVING SKIN CONDITION WITH BIOACTIVE COMPOUND

CROSS-REFERENCE TO RELATED APPLICATION

This non-provisional application claims priority under 35 U.S.C. § 119(a) to Patent Application No. 109126750 filed in Taiwan, R.O.C. on Aug. 6, 2020, the entire contents of which are hereby incorporated by reference.

REFERENCE OF AN ELECTRONIC SEQUENCE LISTING

The contents of the electronic sequence listing (2278-P200378USI_a113_ST25.txt; Size: 4.8 KB; and Date of Creation: Nov. 17, 2020) is herein incorporated by reference in its entirety.

BACKGROUND

Technical Field

The present invention relates to a method for improving a skin condition of a subject in need thereof, and more particularly to a method for improving the skin condition of the subject by administering to the subject a composition including a bioactive compound.

Related Art

Tilapia, with a scientific name of *Oreochromis mossambicus*, has the advantages of fresh and tender meat quality, few small fish bones, easiness in cultivation, low price, high nutrient content, etc., and has become an important source of food protein intake of the public in the society at present.

Tilapia is commonly processed into edible fillets. Two hundred tons of wastes, such as fish heads, fish skin, fish scales, fish tails, fish bones, internal organs and other byproducts are generated during production per one thousand tons of the fillets.

In recent years, in order to reduce resource waste and avoid environment pollution, these related byproducts are gradually valued. In these byproducts, the fish skin is rich in collagen, and is often used for manufacturing processed food, gelatin, scald bandages and the like through secondary processing since its composition structure is similar to that of the human body.

Collagen is a very important protein in the human body, and widely exists in connective tissues. Collagen acts as a main ingredient of tissues such as human body ligaments and eye corneas. In addition, collagen is also a main composition ingredient of an extracellular matrix. Collagen can enable the skin to maintain elasticity. Along with loss of collagen, the skin would also generate wrinkles.

However, collagen cannot be directly absorbed by the human body.

SUMMARY

In view of the aforementioned problem, the present invention provides methods for improving a skin condition of a subject in need thereof by administering to the subject a composition including a bioactive compound, and the bioactive compound is a peptide.

In some embodiments, a method for improving a skin condition of a subject in need thereof including administering to the subject a composition including a bioactive compound is provided. The bioactive compound is a peptide. In addition, the peptide includes at least one amino acid sequence as set forth in SEQ ID NO: 1 to SEQ ID NO: 11. Each of the amino acid sequence is a peptide of the fish skin.

Based on the above, the peptide as the bioactive compound according to any embodiment can be used for preparing the composition improving the skin condition. In addition, the peptide includes at least one amino acid sequence as set forth in SEQ ID NO: 1 to SEQ ID NO: 11. Each of the amino acid sequence is a peptide of the fish skin. In some embodiments, the peptide as the bioactive compound can be used for regulating expression of at least one gene of FBN1 gene, LOX gene, TIMP1 gene and MMP2 gene. In some embodiments, the composition includes a peptide used for regulating at least one gene of FBN1 gene, LOX gene, TIMP1 gene, COL4A1 gene, HAS2 gene, ELN gene and MMP2 gene. The composition can be used for promoting generation of skin collagen, improving density of skin collagen, preventing loss of skin collagen, reducing loss of skin moisture, improving skin elasticity, reducing wrinkles or achieving a combination of these effects.

DETAILED DESCRIPTION

Figure 1:
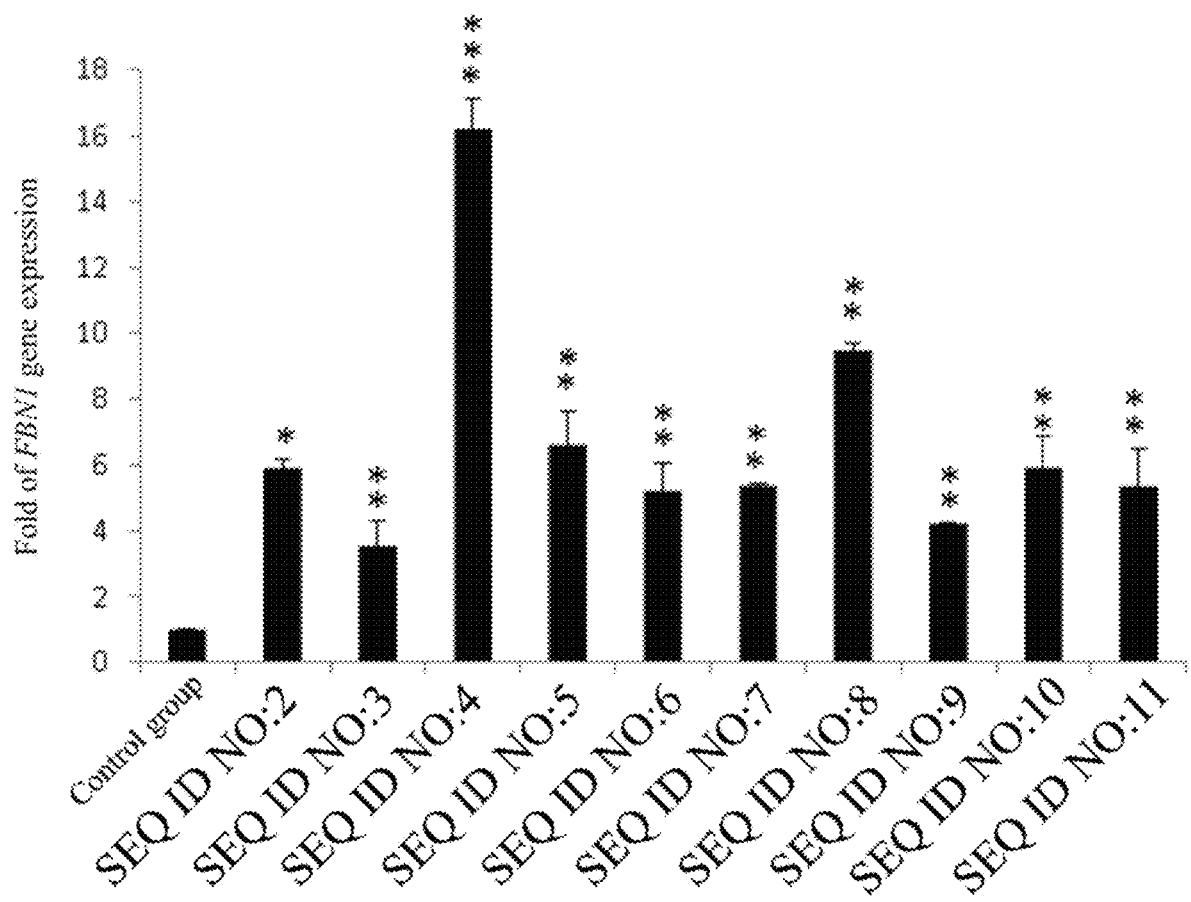
FIG. 1 is a bar chart showing folds of FBN1 gene expression after treatment on human cells by a peptide in accordance with some embodiments of the present invention.

In some embodiments, a peptide used as a bioactive compound can be used for preparing a composition improving the skin condition. The peptide includes at least one amino acid sequence as set forth in SEQ ID NO: 1 to SEQ ID NO: 11. Each of the amino acid sequence is a peptide of fish skin.

It should be understood that the "peptide" contains a plurality of amino acids, the number of which is between that of an amino acid and that of a protein. In addition, the peptide as the bioactive compound may be an "isolated peptide" or a "synthesized peptide." The "isolated peptide" refers to a peptide isolated from an organism or an organism derivative, and this peptide has bioactivity. The "synthesized peptide" refers to a peptide synthesized by an instrument or an experimental operation according to an amino acid sequence of interest, and this peptide has bioactivity.

In some embodiments, the peptide as the bioactive compound can be obtained by isolation from peptides of the fish skin or be synthesized by using an instrument or an experiment. For example, the source of the peptide of the fish skin includes fish skin cells, collagen (called as fish skin collagen hereafter) and fish muscle cells. Because a main ingredient in the fish skin is collagen, fish skin collagen mainly extracted in a process of extracting the fish skin collagen from the fish skin; however, proteins (i.e., fish skin cell proteins) in the fish skin cells and proteins (i.e., fish muscle cell proteins) of the fish muscle cells remaining on the fish skin may also be included. It should be understood that the term "peptide of the fish skin" described herein refers to a peptide including not only collagen as a main ingredient but also peptides of the fish skin cell proteins and the fish muscle cell proteins.

In some embodiments, the fish skin is tilapia skin. Therefore, the peptide as the bioactive compound is a peptide of tilapia skin. The peptide of tilapia skin can include a peptide of at least one of collagen, procollagen, fish skin cell protein and fish muscle cell protein, or a combination thereof. For example, the collagen may be type I collagen, type IV collagen, type V collagen, type VI collagen, type VII collagen, type XII collagen, or type XVIII collagen and the like, and the procollagen may be type I procollagen.

In addition, in some embodiments, the peptide as the bioactive compound may be a group of peptides resulted from mixing any of 11 amino acid sequences as set forth in SEQ ID NO: 1 to SEQ ID NO: 11 through chemical (such as enzymatic hydrolysis treatment) or/and physical (such as purification, isolation, hydrophilic and hydrophobic attraction and polar and non-polar solvents) treatment.

For example, a raw material for collagen peptides of tilapia skin can be isolated to obtain at least one amino acid sequence as set forth in SEQ ID NO: 1 to SEQ ID NO: 11. In addition, the raw material for collagen peptides includes the peptide of the fish skin collagen, the peptide of the fish skin cell proteins and/or the peptide of the fish muscle cell proteins. In an embodiment, the raw material for collagen peptides may be commercially available tilapia fish skin collagen peptide powder (purchased from LAPI, Italy), or collagen peptide powder formed by performing enzymatic hydrolysis treatment and drying on the collagen extracted from tilapia skin.

In some explanatory examples, the peptide as the bioactive compound can be obtained by isolation from tilapia fish skin collagen peptide powder by using an instrument (such as a fast protein liquid chromatography and a high performance liquid chromatography system). In addition, in the above isolation process, at least one amino acid sequence as set forth in SEQ ID NO: 1 to SEQ ID NO: 11 may be isolated by using the properties (physical or chemical properties such as molecular weight, hydrophilic and hydrophobic properties and polar and non-polar properties) of the peptide.

Therefore, when the peptide includes a plurality of amino acid sequences as set forth in SEQ ID NO: 1 to SEQ ID NO: 11, these amino acid sequences can be peptides from the same proteins, or peptides from different proteins. For example, dipeptides including amino acid sequences of SEQ ID NO: 2 and SEQ ID NO: 3 are both from type IV collagen.

In some embodiments, the molecular weight of each of the amino acid sequence is in a range of 700 Da to 1900 Da. In some embodiments, each of the amino acid sequence has 7 to 21 amino acids.

In some embodiments, the peptide as the bioactive compound can be used for regulating the expression of at least one gene. The at least one gene includes at least one gene of FBN1 gene, LOX gene, TIMP1 gene and MMP2 gene. In other words, the peptide can be used for regulating at least one gene of FBN1 gene, LOX gene, TIMP1 gene and MMP2 gene.

It should be understood that the term "regulating the expression of gene(s)" described herein may refer to "promoting the expression of gene(s)" or "inhibiting the expression of gene(s)."

The composition is prepared from the peptide capable of regulating at least one gene of FBN1 gene, LOX gene, TIMP1 gene and MMP2 gene, so that the composition has the capability of regulating at least one gene of FBN1 gene, LOX gene, TIMP1 gene and MMP2 gene.

In some embodiments, when the peptide includes at least one amino acid sequence as set forth in SEQ ID NO: 2 to SEQ ID NO: 11, the peptide can regulate the FBN1 gene, and the composition containing the peptide can be used for promoting the expression of FBN1 gene. For example, when any one or more of amino acid sequences as set forth in SEQ ID NO: 2 to SEQ ID NO: 11 are selected to prepare the composition, the composition can be used for promoting the expression of FBN1 gene for maintaining the extracellular matrix.

In some embodiments, when the peptide includes at least one amino acid sequence as set forth in SEQ ID NO: 2, SEQ ID NO: 5, SEQ ID NO: 9 and SEQ ID NO: 11, the peptide can regulate the LOX gene, and the composition containing the peptide can be used for promoting the expression of LOX gene. For example, when the composition is prepared from any one or more of amino acid sequences as set forth in SEQ ID NO: 2, SEQ ID NO: 5, SEQ ID NO: 9 and SEQ ID NO: 11, the composition can be used for promoting the expression of LOX gene for maintaining hardness and stability of the extracellular matrix.

In some embodiments, when the peptide includes at least one amino acid sequence as set forth in SEQ ID NO: 2, SEQ ID NO: 6, SEQ ID NO: 8, SEQ ID NO: 9 and SEQ ID NO: 11, the peptide can regulate the TIMP1 gene, and the composition containing the peptide can be used for promoting the expression of TIMP1 gene. For example, when the composition is prepared from any one or more of amino acid sequences as set forth in SEQ ID NO: 2, SEQ ID NO: 6, SEQ ID NO: 8, SEQ ID NO: 9 and SEQ ID NO: 11, the composition can be used for promoting the expression of TIMP1 gene.

In some embodiments, when the peptide includes at least one amino acid sequence as set forth in SEQ ID NO: 2, SEQ ID NO: 3, SEQ ID NO: 5 and SEQ ID NO: 10, the peptide can regulate MMP2 gene, and the composition containing the peptide can be used for inhibiting the expression of MMP2 gene for prevention of decomposition of collagen. For example, when the composition is prepared from any one or more of amino acid sequences as set forth in SEQ ID NO: 2, SEQ ID NO: 3, SEQ ID NO: 5 and SEQ ID NO: 10, the composition can be used for inhibiting the expression of MMP2 gene.

In some embodiments, when the peptide includes an amino acid sequence as set forth in SEQ ID NO: 1 to SEQ ID NO: 11, the peptide can regulate at least one gene of FBN1 gene, LOX gene, TIMP1 gene, COL4A1 gene, HAS2 gene, ELN gene and MMP2 gene, and the composition containing the peptide can be used for promoting the expression of at least one gene of FBN1 gene, LOX gene, TIMP1 gene, COL4A1 gene, HAS2 gene and ELN gene, and/or inhibiting the expression of MMP2 gene.

In some embodiments, the composition prepared from the peptide having at least one amino acid sequence as set forth in SEQ ID NO: 1 to SEQ ID NO: 11 can be used for improving the skin condition. For example, the composition prepared from the peptide having at least one amino acid sequence as set forth in SEQ ID NO: 1 to SEQ ID NO: 11 can have at least one of the following effects: promoting generation of skin collagen, improving density of skin collagen, preventing loss of skin collagen, reducing loss of skin moisture, improving skin elasticity and reducing wrinkles.

For example, when the composition includes the peptide for regulating at least one gene of FBN1 gene and COL4A1 gene, the composition can be used for promoting generation of skin collagen and improving density of skin collagen. When the composition includes the peptide for regulating at least one gene of TIMP1 gene and MMP2 gene, the composition can be used for preventing loss of skin collagen. When the composition includes the peptide for regulating the HAS2 gene, the composition can be used for reducing loss of skin moisture. When the composition includes the peptide for regulating at least one gene of FBN1 gene, LOX gene and ELN gene, the composition can be used for improving skin elasticity. When the composition includes the peptide for regulating at least one gene of FBN1 gene, LOX gene, TIMP1 gene, COL4A1 gene, HAS2 gene, ELN gene and MMP2 gene, the composition can be used for reducing wrinkles.

In some embodiments, the composition prepared from the peptide having at least one amino acid sequence as set forth in SEQ ID NO: 1 to SEQ ID NO: 11 can be a food composition, a health care food composition, a pharmaceutical composition, etc. For example, the composition prepared from the peptide having at least one amino acid sequence as set forth in SEQ ID NO: 1 to SEQ ID NO: 11 can be oral collagen peptide powder. Therefore, by taking the composition, the peptide included therein can regulate the gene expression of skin cells for improving the skin cell conditions.

Example 1: Preparation of the Isolated Peptides

Firstly, 100 mg of tilapia fish skin collagen peptide powder (purchased from LAPI, Italy) was weighed and dissolved into 5 mL of a buffer solution A to obtain a collagen peptide solution. The buffer solution A was prepared from a 50 mM Tris/HCl buffer solution (pH 8.0) and 100 mM sodium chloride (NaCl).

Then, a fast protein liquid chromatography instrument (FPLC purification instrument, from ÄKTA GE Healthcare Life Sciences, and called as a purification instrument hereafter) was used for coarse isolation of the collagen peptide solution, so as to obtain a primary isolated peptide mixture. The separation column disposed in the purification instrument was a molecular sieve colloid purification column (sephadex G-25, 2.6 cm×10 cm, 53 mL). A flow rate of the purification instrument was set to be 1 mL/min, and the ultraviolet light had wavelengths of 220 nm and 280 nm. The primary isolated peptide mixture having an absorption peak corresponding to 5 kDa or lower was subjected to lypholization at −80° C. (instrument brand: EYELA, model: FD-1000) for 12 h, so as to obtain a solid primary isolated peptide mixture.

30 mg of the solid primary isolated peptide mixture was dissolved into 2 mL of deionized water containing 0.1% trifluoroacetic acid (TFA), so as to obtain a pre-isolated peptide mixture. Then, the pre-isolated peptide mixture was separated by a high-performance liquid chromatography (HPLC) system (machine type: Hitachi Chromaster HPLC system; brand: Hitachi, Tokyo, Japan) (called as an HPLC system hereafter), so as to obtain a plurality of groups of isolated peptides. A molecular sieve C18 high-pressure column (model: TSKgel G2000SWXL; brand: Tosoh, 30 cm×7.8 mm, 5 μm) was disposed in the HPLC system. In set values of the HPLC system, a buffer solution A (i.e., a solution with 0.1% TFA dissolved into 100% deionized water) and a buffer solution B (i.e., a solution with 0.1% TFA dissolved into 100% ACN) were mixed according to a separation gradient. The separation gradient was 5% acetonitrile (ACN)/0.1% TFA to 100% ACN/0.1% TFA (i.e., the concentration gradient of the ACN was raised from 5% to 100% in a 0.1% TFA solution environment), the flow rate was set to be 1 mL/min, and the column temperature was set to be 40° C.

Therefore, the peptide in the primary isolated peptide mixture could be eluted out along with the HPLC solutions with different polarities and molecular weights, and the groups of isolated peptides were obtained. In addition, the groups of isolated peptides were subjected to lypholization at −80° C. (instrument brand: EYELA, model: FD-1000) for 12 h, so as to obtain a plurality of groups of solid isolated peptides.

Example II: Peptide Identification

The plurality of groups of isolated peptides in Example I were subjected to protein identification. Firstly, after reaching a concentration of 20 mg/mL by addition of deionized water, the groups of solid isolated peptides were subjected to protein identification by a liquid chromatography mass spectrometer (LC-MS/MS). LC-MS/MS was a quadrupole-time-of-flight tandem mass spectrometer system (Q-TOF). The model of a liquid chromatography system (LC system) was UltiMate 3000 RSLCnano LC Systems (brand: Thermo Fisher Scientific), and the model of the mass spectrometer was TripleTOF®6600 System (brand: Applied Biosystems Sciex).

The separation column disposed in the liquid chromatography system was a C18 separation column (Acclaim Pep-Map C18, 75 µm I.D.×25 cm nanoViper, 2 µm, 100 Å (Thermo Fisher Scientific)). A solution system used by the liquid chromatography mass spectrometer was a buffer solution A (i.e., a solution with 0.1% TFA dissolved into 100% deionized water) and a buffer solution B (i.e., a solution with 0.1% TFA dissolved into 100% ACN). A separation gradient set by the liquid chromatography mass spectrometer was 5% to 90% of the buffer solution B at the flow rate of 300 nL/min in 30 min.

In set values of the mass spectrometer, survey scan was set to scan all ionized isolated peptides in a range of 400 m/z (mass-to-charge ratio) to 1200 m/z. In an information dependent acquisition (CID) mode, a detection range of the peptide was set to be 100-5000 Da. Then, these isolated peptides were analyzed, and a plurality of MS/MS spectra was correspondingly generated. These MS/MS spectra were retrieved in databases (NCBI and UniProt) by a Mascot analysis program, so as to obtain the amino acid sequences and identification information of these isolated peptides, as shown in Table 1 and Table 2.

TABLE 1

| Sequence number | Sequence | Molecular weight |
| --- | --- | --- |
| SEQ ID NO: 1 | GFDIGFI | 767.39 |
| SEQ ID NO: 2 | GLPGVQGNI | 855.43 |
| SEQ ID NO: 3 | IGIFGQTGPPGE | 1171.59 |
| SEQ ID NO: 4 | PGPMGPMGINGA | 1097.5 |
| SEQ ID NO: 5 | AVNGLTLAGGRGLNTGAALT | 1826 |
| SEQ ID NO: 6 | ALVQNREGP | 984.5 |
| SEQ ID NO: 7 | NGLPGSPGLP GRQGE | 1435.71 |
| SEQ ID NO: 8 | PGQPGLSGVPGADGKPGLPGP | 1853.96 |
| SEQ ID NO: 9 | MFGKDVW | 881.41 |
| SEQ ID NO: 10 | DQGIRLL | 814.45 |
| SEQ ID NO: 11 | QRGEPGPNGAV | 1082.5 |

As shown in Table 1, the molecular weight of the amino acid sequences of the isolated peptide was in a range of 700 Da to 1900 Da, and the isolated peptide had 7 to 21 amino acids.

TABLE 2

| Sequence number | Identification information |
| --- | --- |
| SEQ ID NO: 1 | Collagen, type I |
| SEQ ID NO: 2 | Collagen, type IV |
| SEQ ID NO: 3 | Collagen, type IV |
| SEQ ID NO: 4 | Collagen, type V |
| SEQ ID NO: 5 | Collagen, type VI |

TABLE 2-continued

| Sequence number | Identification information |
| --- | --- |
| SEQ ID NO: 6 | Collagen, type VII |
| SEQ ID NO: 7 | Collagen, type XII |
| SEQ ID NO: 8 | Collagen, type XVIII |
| SEQ ID NO: 9 | N-acetylglucosamine-1-phosphotransferase subunits alpha/beta |
| SEQ ID NO: 10 | Plectin b |
| SEQ ID NO: 11 | Procollagen, type I |

In addition, as shown in Table 2, the amino acid sequence of the isolated peptide was a peptide of tilapia skin. SEQ ID NO: 1 to SEQ ID NO: 8 and SEQ ID NO: 11 were peptides of at least one type of collagen of tilapia skin. SEQ ID NO: 9 was a peptide of a cytase. SEQ ID NO: 10 was an intracellular protein. For example, SEQ ID NO: 1 to SEQ ID NO: 8 were peptides of the collagen. SEQ ID NO: 11 was a peptide of procollagen. SEQ ID NO: 9 was a peptide of N-acetylglucosamine-1-phosphotransferase subunits alpha/beta. SEQ ID NO: 10 was a peptide of Plectin b. Therefore, a raw material for tilapia skin collagen peptides includes amino acid sequences of 11 types of isolated peptides as in SEQ ID NO: 1 to SEQ ID NO: 11.

Example III: Peptide Synthesis

In order to verify the effects of the amino acid sequences of the 11 types of isolated peptides on skin cells, synthesized peptides were prepared in Example III according to the amino acid sequences identified in Example II (i.e., SEQ ID NO: 1 to SEQ ID NO: 11). The synthesis was a solid phase synthesis (Fmoc-Solid Phase Peptide Synthesis). In addition, the instrument was a peptide synthesis instrument (model: Focus XC III 0, America; brand: AAPPTEC).

The amino acid sequence of SEQ ID NO: 2 was taken as an example hereafter. The amino acid sequence of SEQ ID NO: 2 is Gly-Leu-Pro-Gly-Val-Gln-Gly-Asn-Ile.

Step (1): Firstly, resin was put into a reaction tube and soaked in 15 mL of dichloromethane (DCM) per 1 g of resin for 30 min so that the resin expanded therein.

Step (2): The dichloromethane in the reaction tube was removed. According to a proportion of 15 mL of 20% piperidine dimethylformamide (piperidine DMF) per 1 g of resin, reaction was performed with the resin in piperidine DMF for 5 min. Then, solvent in the reaction tube was removed. Then, according to a proportion of 15 mL of 20% piperidine dimethylformamide solution per 1 g of resin, reaction was performed with the resin again for 15 min, so as to remove protecting groups on the resin, and obtain deprotected resin.

Step (3): After the solution in the reaction tube was removed again, a few resin particles were taken out from the reaction tube for characterization. Firstly, the resin was washed for three times by ethanol, and one drip of ninhydrin solution and one drip of phenol solution were added. Heating was performed for 5 min at 105° C. to 110° C. When the ninhydrin solution and the phenol solution reacted with the resin and became dark blue, the reaction was positive, suggesting that the resin in the reaction tube was deprotected and could be combined with amino acids.

Step (4): According to a proportion of 10 mL of dimethylformamide per 1 g of resin, the deprotected resin was added to the reaction tube and repeatedly washed for 6 times.

Step (5): After three-time excessive protected glycine (Fmoc-Gly) and three-time excessive hydroxybenzotriazole (HOB$_t$) were dissolved by a small amount of dimethylformamide, they were added into the reaction tube containing the deprotected resin to react for 90 min.

Step (6): After reacting for 90 min, according to a proportion of 10 mL of dimethylformamide per 1 g of resin, the resin attached with amino acids was repeatedly washed for 3 times.

Then, Step (2) to Step (6) were repeated until other amino acids (Leu, Pro, Gly, Val, Gln, Gly, Asn, and Ile) were sequentially attached to form a primary synthesized peptide with an amino acid sequence of SEQ ID NO: 2.

Step (7): According to a proportion of 10 mL of dimethylformamide to per 1 g of resin, the primary synthesized peptide was repeatedly washed for 3 times. Then, according to a proportion of 10 mL of dichloromethane per 1 g of resin, the primary synthesized peptide was washed for 3 times. Finally, according to a proportion of 10 mL of ethanol to per 1 g of resin, the primary synthesized peptide was washed for 3 times.

Step (8): The washed primary synthesized peptide was reacted with 10 g of lysis solution (86% of trifluoroacetic acid, 4% of thioanisole, 3% of water, 5% of ethanedithiol (EDT) and 2% of phenol) for 120 min, so as to separate the primary synthesized peptide from the resin.

Step (9): By a sandbag funnel, the lysis solution containing the primary synthesized peptide was separated from the resin. Then, the lysis solution containing the primary synthesized peptide was added to diethyl ether with a volume of eight times of the above lysis solution. Next, suction filtering separation was performed by a Buchner funnel so as to obtain primary synthesized peptide and the lysis solution. After evaporating the diethyl ether containing the lysis solution, the primary synthesized peptide was washed for three times by the diethyl ether. The primary synthesized peptide was solid. In addition, after the diethyl ether was volatilized at a room temperature, the dried primary synthesized peptide was obtained.

Step (10): After 1 mg of dried primary synthesized peptide was re-dissolved by 0.5 mL of deionized water, 20 mL of re-dissolved primary synthesized peptide was isolated and purified by an HPLC system (machine type: Hitachi Chromaster HPLC system; brand: Hitachi, Tokyo, Japan), so as to obtain a pure synthesized peptide. A C18 column (brand: Gemini-NX) was disposed in the HPLC system. A detection wavelength was set to be 220 nm. In addition, in the HPLC system, a buffer solution A (i.e., a solution with 0.1% TFA dissolved into 100% deionized water) and a buffer solution B (i.e., a solution with 0.1% TFA dissolved into 100% ACN) were mixed according to a linear separation gradient, to elute and separate out the synthesized peptide. A set value of the separation gradient was a linear gradient from 10% of the buffer solution B to 90% of ACN (dissolved into 0.1% TFA). The flow rate was set to be 1 mL/min. The separation time was set to be 30 min. In addition, a result that the purities of the synthesized peptides all reached 95% or above could be obtained by calculating the peak area of each synthesized peptide according to an HPLC chromatography. Therefore, the synthesized peptide including the amino acid sequence of SEQ ID NO: 2 could be obtained.

Likewise, other amino acid sequences (i.e., SEQ ID NO: 1, and SEQ ID NO: 3 to SEQ ID NO: 11) could also be treated according to the above process. After Step (1), the above Step (2) to Step (6) were repeatedly performed until the amino acids were connected to form the corresponding amino acid sequences. Then, Step (7) to Step (10) were performed for washing and purification, so as to obtain purify (the purity being up to 95%) synthesized peptide (i.e., SEQ ID NO: 1 and SEQ ID NO: 3 to SEQ ID NO: 11).

In order to confirm the effect of each of the amino acid sequences on gene expression in cells, human fibroblasts (CCD-966SK) and individual peptides were co-cultured, and then, gene expression in the cells was analyzed. 11 types of synthesized peptides were respectively subjected to cell experiments. In addition, the amino acid sequences of 11 types of synthesized peptides were respectively SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11. Hereafter, the sequence numbers SEQ ID NO: 1 to SEQ ID NO: 11 will be referred to as groups.

(1) Experiment Materials and Experiment Groups

Cell gene expression test refers to that after the human fibroblasts (purchased from Food Industry Research and Development Institute) and samples to be tested (such as peptides or compositions) were co-cultured, then, RNA in the cells was collected for analysis. Referring to Table 3, the gene expression test groups were divided into 13 groups. 11 groups therein were peptide experiment groups (Experiment group A to Experiment group K), 1 group was a composition experiment group (Experiment group L), and 1 group was a control group. In addition, each group was co-cultured with $1 \times 10^5$ human fibroblasts in a cell culture plate containing 2 mL of cell culture medium (X-VIVO™ 10). Experiment group A to Experiment group K respectively corresponded to 11 groups of peptide experiment groups of 11 types of synthesized peptides (SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11) prepared according to Example III. Experiment group L was a composition experiment group added with the composition. In addition, the composition was identified in Example II to be tilapia fish skin collagen peptide powder (purchased from LAPI, Italy) including 11 types of peptides (i.e., SEQ ID NO: 1, SEQ ID NO: 2, SEQ ID NO: 3, SEQ ID NO: 4, SEQ ID NO: 5 and SEQ ID NO: 6). No peptide or composition was added in Control group.

TABLE 3

| Gene expression test group | | Cell culture medium (2 mL) | Cells to be tested ($1 \times 10^5$) | Samples to be tested |
| --- | --- | --- | --- | --- |
| SEQ ID NO: 1 peptide experiment group | Experiment group A | X-VIVO™ 10 | Human fibroblasts | 25 μg of SEQ ID NO: 1 peptide was added |
| SEQ ID NO: 2 peptide experiment group | Experiment group B | X-VIVO™ 10 | Human fibroblasts | 25 μg of SEQ ID NO: 2 peptide was added |

TABLE 3-continued

| Gene expression test group | Cell culture medium (2 mL) | Cells to be tested (1 × 10$^5$) | Samples to be tested |
|---|---|---|---|
| SEQ ID NO: 3 peptide experiment group | Experiment group C | X-VIVO™ 10 | Human fibroblasts | 25 μg of SEQ ID NO: 3 peptide was added |
| SEQ ID NO: 4 peptide experiment group | Experiment group D | X-VIVO™ 10 | Human fibroblasts | 25 μg of SEQ ID NO: 4 peptide was added |
| SEQ ID NO: 5 peptide experiment group | Experiment group E | X-VIVO™ 10 | Human fibroblasts | 25 μg of SEQ ID NO: 5 peptide was added |
| SEQ ID NO: 6 peptide experiment group | Experiment group F | X-VIVO™ 10 | Human fibroblasts | 25 μg of SEQ ID NO: 6 peptide was added |
| SEQ ID NO: 7 peptide experiment group | Experiment group G | X-VIVO™ 10 | Human fibroblasts | 25 μg of SEQ ID NO: 7 peptide was added |
| SEQ ID NO: 8 peptide experiment group | Experiment group H | X-VIVO™ 10 | Human fibroblasts | 25 μg of SEQ ID NO: 8 peptide was added |
| SEQ ID NO: 9 peptide experiment group | Experiment group I | X-VIVO™ 10 | Human fibroblasts | 25 μg of SEQ ID NO: 9 peptide was added |
| SEQ ID NO: 10 peptide experiment group | Experiment group J | X-VIVO™ 10 | Human fibroblasts | 25 μg of SEQ ID NO: 10 peptide was added |
| SEQ ID NO: 11 peptide experiment group | Experiment group K | X-VIVO™ 10 | Human fibroblasts | 25 μg of SEQ ID NO: 11 peptide was added |
| Composition experiment group | Experiment group L | X-VIVO™ 10 | Human fibroblasts | 200 mg of composition was added |
| Control group | | X-VIVO™ 10 | Human fibroblasts | No peptide or composition was added |

(II) Experiment Design

For each group of peptide experiment groups (corresponding to Experiment group A to Experiment group K), according to a proportion of 12.5 μg of synthesized peptide per 1 mL of cell culture medium, the human fibroblasts were cultured for 24 h at 37° C. For the composition experiment group (corresponding to Experiment group L), according to a proportion of 100 mg of composition per 1 mL of cell culture medium, the human fibroblasts were cultured for 24 h. For Control group, no peptide was added, and the human fibroblasts were cultured for 24 h in a pure cell culture medium. In addition, after culture for 24 h, the peptide-containing cell culture medium or the pure culture medium was removed from each group, and cells in each group were washed by a phosphate buffer solution (PBS) so as to remove the residual culture medium. The washed cells were spun down and were subjected to cell lysis by a cell lysis solution (purchased from Geneaid company, Taiwan). Then, RNA in each group of cells was extracted by an RNA extraction kit (purchased from Geneaid company, Taiwan). Next, the extracted RNA was subjected to inverse transcription to obtain cDNA by a cDNA synthesis reagent (purchased from Geneaid company, Taiwan). In addition, the intracellular gene expression was observed by a polymerase chain reaction (PCR) instrument using different primers (as shown in Table 3). In addition, the primers firstly reacted by a green fluorescent dye of SYBR green dye (Applied Biosystem), and quantification of gene expression was performed by a 2-ΔΔCt method. It should be noted that the gene expression in the drawings corresponding to the experiments was shown in relative fold or percentage, wherein standard deviations were calculated by an STDEV formula of Excel software, and statistically significant differences were analyzed by one-tailed student t-test in the Excel software. In the drawings, "*" represents $p<0.05$, "" represents $p<0.01$, and "*" represents $p<0.001$. More "*" represents more significant statistical differences.

TABLE 4

| Primer name | Sequence number | Sequence |
|---|---|---|
| FBN1-F | SEQ ID NO: 12 | TTTAGCGTCCTACACGAGCC |
| FBN1-R | SEQ ID NO: 13 | CCATCCAGGGCAACAGTAAGC |
| LOX-F | SEQ ID NO: 14 | CGGCGGAGGAAAACTGTCT |
| LOX-R | SEQ ID NO: 15 | TCGGCTGGGTAAGAAATCTGA |
| TIMP1-F | SEQ ID NO: 16 | AGAGTGTCTGCGGATACTTCC |
| TIMP1-R | SEQ ID NO: 17 | CCAACAGTGTAGGTCTTGGTG |
| MMP2-F | SEQ ID NO: 18 | GATACCCCTTTGACGGTAAGGA |
| MMP2-R | SEQ ID NO: 19 | CCTTCTCCCAAGGTCCATAGC |
| COL4A4-F | SEQ ID NO: 20 | CTGGGTGCTGTGTGTTTTGA |
| COL4A4-R | SEQ ID NO: 21 | TGAGTCTTGTTTTGCCCTGC |
| HAS2-F | SEQ ID NO: 22 | CGGTGCTCCAAAAAGGCAAA |
| HAS2-R | SEQ ID NO: 23 | ACACAATGAGTTGGGCGAGA |
| ELN-F | SEQ ID NO: 24 | GCTAAGGCAGCCAAGTATGG |
| ELN-R | SEQ ID NO: 25 | CACCTGGGACAACTGGAATC |

Firstly, 11 groups of peptide experiment groups (i.e., Experiment group A to Experiment group K) and a control group were subjected to gene expression analysis of FBN1 gene (GeneID: 2200), LOX gene (GeneID: 4015), TIMP1 gene (GeneID: 7076) and MMP2 gene (GeneID: 4313), as shown in FIG. 1 to FIG. 4.

It should be understood that as listed in Table 3, a group marked as SEQ ID NO: 1 in the drawings equals to Experiment group A marked hereafter, and so on. Groups marked as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and SEQ ID NO: 11 in the drawings respectively and correspondingly equal to Experiment group A to Experiment group K marked hereafter.

(III) Expression Analysis of FBN1 Gene in Peptide Experiment Groups and Control Group FBN1 gene is a coding gene of human fibroblast Fibrillin-1 (FBN1) protein. By observing the expression of FBN1 gene, the expression of FBN1 protein can be analyzed. When the FBN1 gene expression is increased, the amount of RNA transcribed from the FBN1 gene is increased. It also represents that the content of protein translated from the RNA is increased. The FBN1 protein is a glycoprotein existing in the extracellular matrix, and can form microfilaments, so that the connective tissues have elasticity. When the expression of FBN1 protein in the corium layer is reduced, the quantity of microfilaments in the corium layer would be affected. In addition, microfilaments provide the tracks for guiding assembly of elastic fiber; so when the content of the FBN1 protein is reduced, the assembly and synthesis of elastic fiber would be affected, and skin elasticity would thus be affected.

Referring to FIG. 1, the FBN1 gene expression in the peptide experiment groups (each peptide experiment group was presented by the sequence number in the drawing) and the control group was tested by FBN1-F (SEQ ID NO: 12) and FBN1-R (SEQ ID NO: 13) primers. The results showed that the FBN1 gene expression of 10 peptide experiment groups: Experiment group B (SEQ ID NO: 2), Experiment group C (SEQ ID NO: 3), Experiment group D (SEQ ID NO: 4), Experiment group E (SEQ ID NO: 5), Experiment group F (SEQ ID NO: 6), Experiment group G (SEQ ID NO: 7), Experiment group H (SEQ ID NO: 8), Experiment group I (SEQ ID NO: 9), Experiment group J (SEQ ID NO: 10) and Experiment group K (SEQ ID NO: 11) was significantly upregulated as compared with that of Control group. For example, the FBN1 gene expression level in Experiment group B was about 6 folds of the FBN1 gene expression level in Control group. The FBN1 gene expression level in Experiment group C was about 3 folds of the FBN1 gene expression level in Control group. The FBN1 gene expression level in Experiment group D was about 16 folds of the FBN1 gene expression level in Control group. The FBN1 gene expression level in Experiment group E was about 6 folds of the FBN1 gene expression level in Control group. The FBN1 gene expression level in Experiment group F was about 5 folds of the FBN1 gene expression level in Control group. The FBN1 gene expression level in Experiment group G was about 5 folds of the FBN1 gene expression level in Control group, but was a little higher than that in Experiment group F. The FBN1 gene expression level in Experiment group H was about 9 folds of the FBN1 gene expression level in Control group. The FBN1 gene expression level in Experiment group I was about 4 folds of the FBN1 gene expression level in Control group. The FBN1 gene expression level in Experiment group J was about 6 folds of the FBN1 gene expression level in Control group. The FBN1 gene expression level in Experiment group K was about 5 folds of the FBN1 gene expression level in Control group. Therefore, when the peptide included SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or a combination thereof, it can be used for promoting the expression of FBN1 gene, and improving skin elasticity.

10 types of amino acid sequences as set forth in SEQ ID NO: 2 to SEQ ID NO: 11 all have the capability of promoting expression of the FBN1 gene, so that a composition prepared from at least one amino acid sequence therein can also be used for promoting expression of the FBN1 gene. In addition, the composition can be used for promoting generation of skin collagen, improving density of skin collagen, improving skin elasticity, reducing wrinkles or achieving a combination of these effects.

(IV) Expression Analysis of LOX Gene in Peptide Experiment Groups and Control Group LOX gene is a coding gene of a lysyl oxidase (LOX). By observing the LOX gene expression, the LOX protein expression can be analyzed. Therefore, the increase in expression level of the LOX gene suggests that the amount of RNA transcribed from the LOX gene is increased, and it also represents that the content of protein translated from the RNA is increased. The content of elastic protein in the elastic fiber reaches 90%, and the elastic protein is synthesized in a soluble elastic proteinogen monomer and secreted to the outside of the cells. After being combined with elastic protein binding proteins, the elastic protein would be transferred into a framework of microfiber, and saccharification reaction is performed through LOX protein or LOX protein-like enzymes. The elastic protein monomers are mutually coagulated and crosslinked into linear or spherical types by saccharification reaction to finally form insoluble elastic protein polymers, and are converted into a crosslinked form. Therefore, the polymer has good compliance and resilience. An elastic property is given to the elastic fiber, and skin elasticity is affected.

Figure 2:
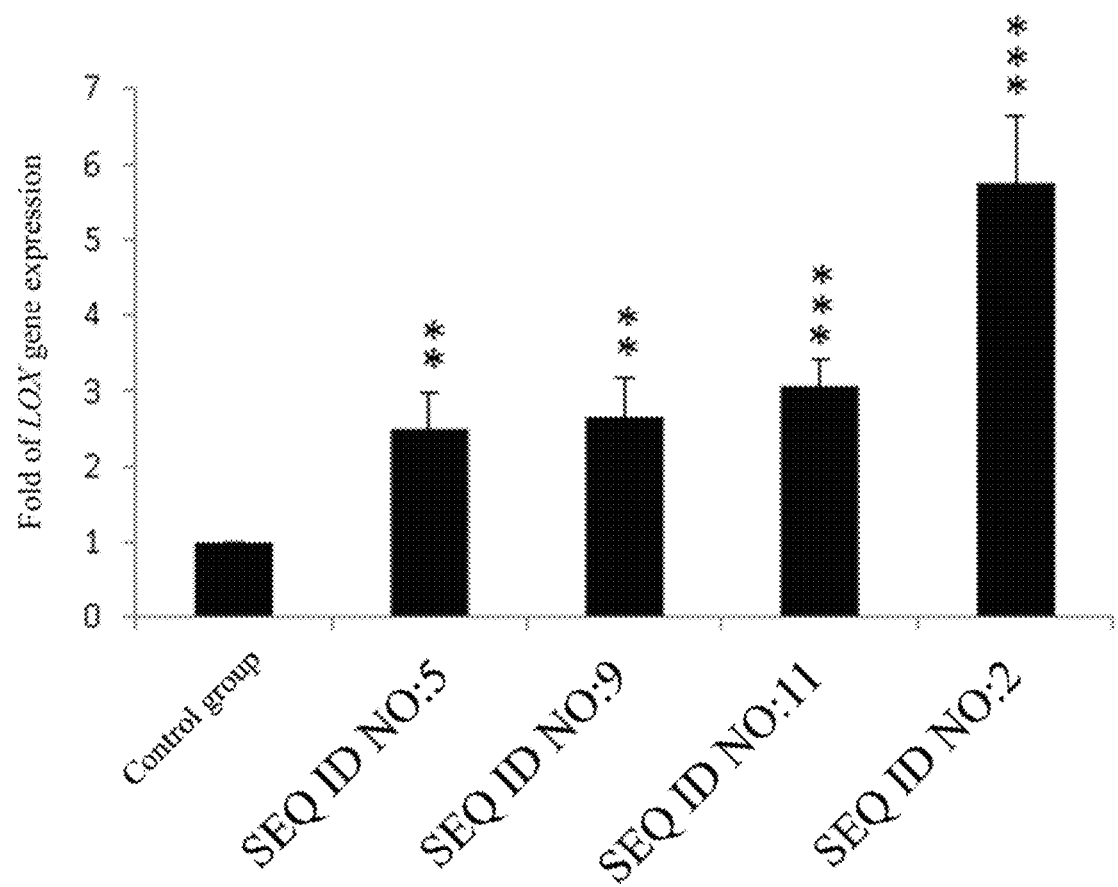
FIG. 2 is a bar chart showing folds of LOX gene expression after treatment on human cells by a peptide in accordance with some embodiments of the present invention.

Referring to FIG. 2, the LOX gene expression in the peptide experiment groups (each peptide experiment group was represented by the sequence number in the drawing) and Control group was tested by LOX-F (SEQ ID NO: 14) and LOX-R (SEQ ID NO: 15) primers. The results showed that the LOX gene expression of 4 peptide experiment groups: Experiment group B (SEQ ID NO: 2), Experiment group E (SEQ ID NO: 5), Experiment group I (SEQ ID NO: 9) and Experiment group K (SEQ ID NO: 11) was significantly upregulated as compared with that of Control group. For example, the LOX gene expression level in Experiment group B was about 5.7 folds of the LOX gene expression level in Control group. The LOX gene expression level in Experiment group E was about 2.5 folds of the LOX gene expression level in Control group. The LOX gene expression level in Experiment group I was about 2.5 folds of the LOX gene expression level in Control group, and was a little higher than that of Experiment group E. The LOX gene expression level in Experiment group K was about 3 folds of the LOX gene expression level in Control group. Therefore, when the peptide included SEQ ID NO: 2, SEQ ID NO: 5, SEQ ID NO: 9, SEQ ID NO: 11 or a combination thereof, it can be used for promoting the expression of LOX gene, and improving skin elasticity.

4 types of amino acid sequences as set forth in SEQ ID NO: 2, SEQ ID NO: 5, SEQ ID NO: 9 and SEQ ID NO: 11 all have the capability of promoting expression of the LOX gene expression, so that a composition prepared from at least one amino acid sequence therein can also be used for promoting expression of the LOX gene expression. In addition, the composition can be used for promoting generation of skin collagen, improving density of skin collagen, improving skin elasticity, reducing wrinkles or achieving a combination of these effects.

(V) Expression Analysis of TIMP1 Gene in Peptide Experiment Groups and Control Group TIMP1 gene is a coding gene of a tissue inhibitor of metalloproteinases 1, (TIMP1). By observing the TIMP1 gene expression, the TIMP1 protein expression can be analyzed. When the TIMP1 gene expression is increased, the amount of RNA transcribed from the TIMP1 gene is increased, and it also represents that the content of protein translated from the RNA is increased. The TIMP1 protein has an anti-collagenase effect, and thus has an effect of protecting skin collagen from degradation.

Figure 3:
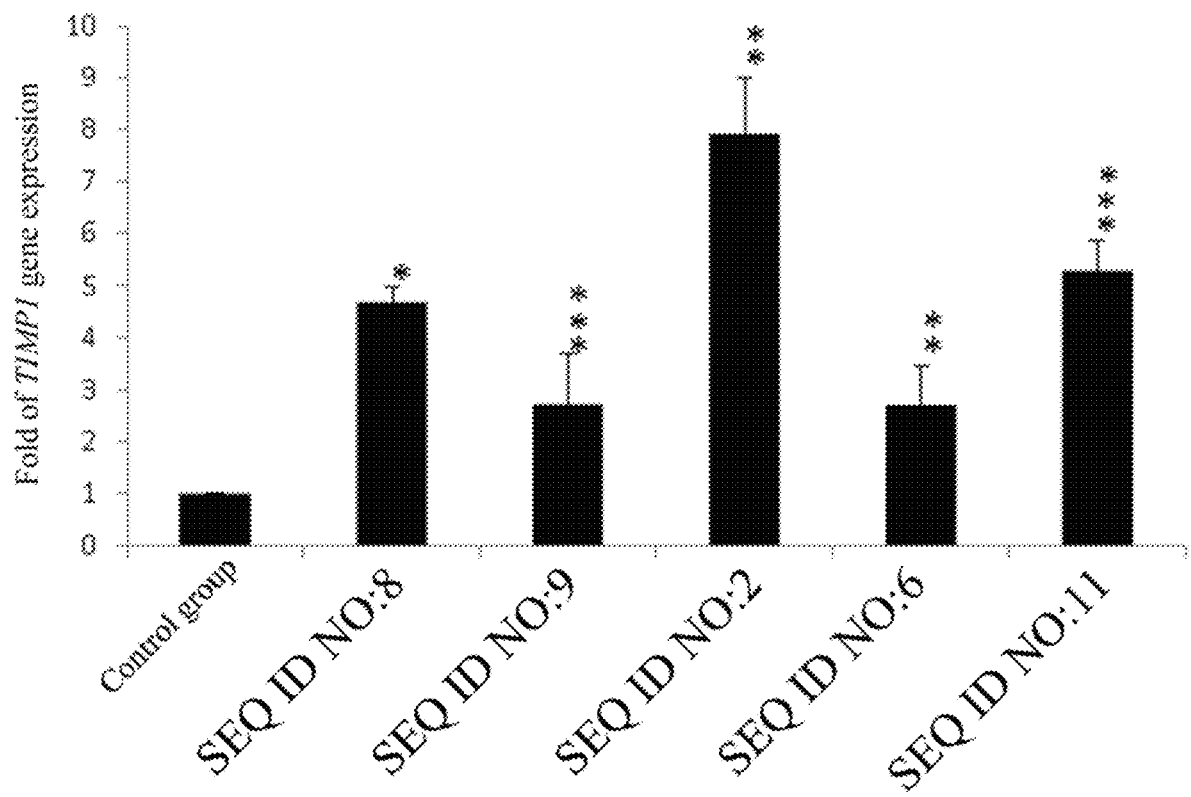
FIG. 3 is a bar chart showing folds of TIMP1 gene expression after treatment on human cells by a peptide in accordance with some embodiments of the present invention.

Referring to FIG. 3, the TIMP1 gene expression of the peptide experiment groups (each peptide experiment group was represented by the sequence number in the drawing) and Control group was tested by TIMP1-F (SEQ ID NO: 16) and TIMP1-R (SEQ ID NO: 17) primers. The results showed that the TIMP1 gene expression of 5 peptide experiment groups: Experiment group B (SEQ ID NO: 2), Experiment group F (SEQ ID NO: 6), Experiment group H (SEQ ID NO: 8), Experiment group I (SEQ ID NO: 9) and Experiment group K (SEQ ID NO: 11) was significantly upregulated as compared with that of Control group. For example, the TIMP1 gene expression level in Experiment group B was about 7.8 folds of the TIMP1 gene expression level in Control group. The TIMP1 gene expression level in Experiment group F was about 3 folds of the TIMP1 gene expression level of Control group. The TIMP1 gene expression level in Experiment group H was about 5 folds of the TIMP1 gene expression level in Control group. The TIMP1 gene expression level in Experiment group I was about 3 folds of the TIMP1 gene expression level in Control group. The TIMP1 gene expression level in Experiment group K was about 5 folds of the TIMP1 gene expression level in Control group. Therefore, when the peptide included SEQ ID NO: 2, SEQ ID NO: 6, SEQ ID NO: 8, SEQ ID NO: 9 and SEQ ID NO: 11 or a combination thereof, it can be used for promoting the expression of TIMP1 gene, and preventing the loss of skin collagen.

5 amino acid sequences as set forth in SEQ ID NO: 2, SEQ ID NO: 6, SEQ ID NO: 8, SEQ ID NO: 9 and SEQ ID NO: 11 all have the capability of promoting expression of the TIMP1 gene expression, so that a composition prepared from at least one amino acid sequence therein can also be used for promoting expression of the TIMP1 gene expression. In addition, the composition can be used for preventing loss of skin collagen, reducing wrinkles or achieving a combination of these effects.

(VI) Expression Analysis of MMP2 Gene in Peptide Experiment Groups and Control Group MMP2 gene is a coding gene of a matrix metalloproteinase-2 (MMP2). By observing the MMP2 gene expression, the MMP2 protein expression can be analyzed. When the MMP2 gene expression is decreased, the quantity of the RNA transcribed by the MMP2 gene is decreased, and it also represents that the content of protein translated by the RNA is decreased. The extracellular matrix structure change and the maintained dynamic balance are affected by zinc-dependent endopeptidase, so that the relevant endopeptidase is a matrix metalloproteinase (MMP) and an MMP tissue inhibitor. In addition, the MMP protein can degrade the elastic fiber protein. For example, there are 8 types of known MMP proteins (such as MMP2, MMP3, MMP7, MMP9, MMP10, MMP12, MMP13 and MMP14). The MMP2, MMP7, MMP9, MMP10, MMP12 and MMP14 proteins can all degrade the insoluble elastic protein into soluble peptides. The MMP2, MMP3, MMP9, MMP12 and MMP13 proteins can all decompose and metabolize fibrillin microfiber and peptides. Therefore, degradation of the elastic fiber protein can be prevented by inhibiting the MMP2 protein expression. The loss of collagen is prevented.

Figure 4:
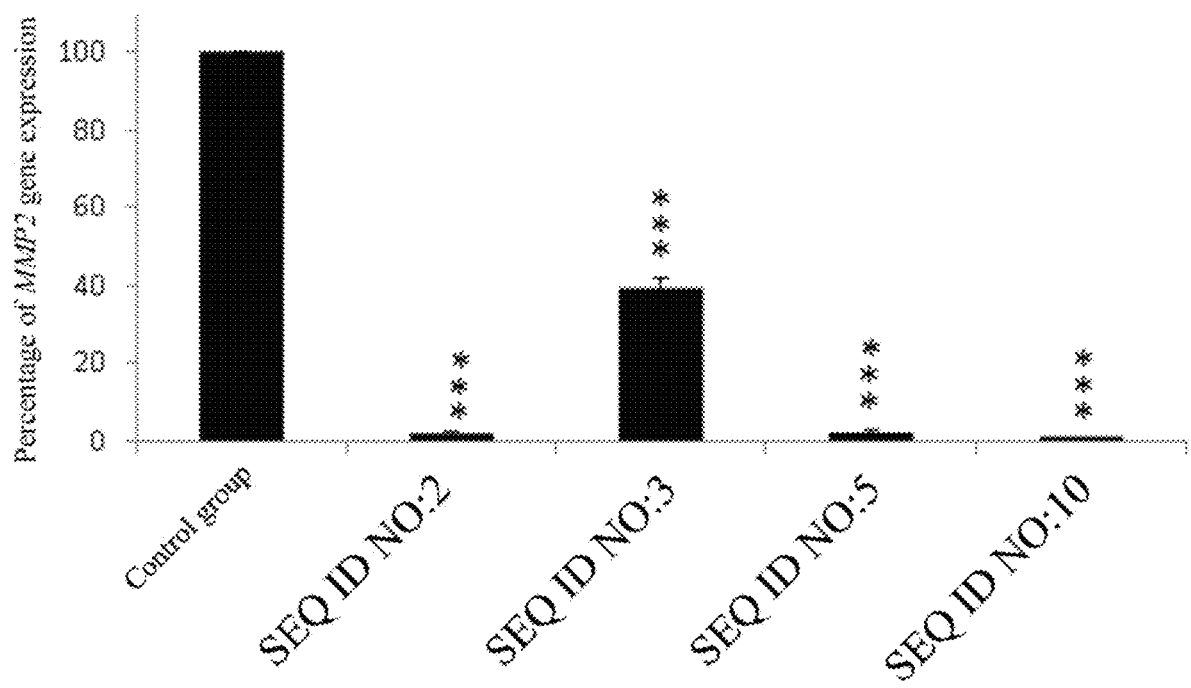
FIG. 4 is a bar chart showing percentages of MMP2 gene expression after treatment on human cells by a peptide in accordance with some embodiments of the present invention.

Referring to FIG. 4, the MMP2 gene expression of the peptide experiment groups (each peptide experiment group was represented by the sequence number in the drawing) and Control group was tested by MMP2-F (SEQ ID NO: 18) and MMP2-R (SEQ ID NO: 19) primers. The results showed that the MMP2 gene expression of 4 peptide experiment groups: Experiment group B (SEQ ID NO: 2), Experiment group C (SEQ ID NO: 3), Experiment group E (SEQ ID NO: 5) and Experiment group J (SEQ ID NO: 10) was significantly downregulated as compared with that of Control group. For example, the MMP2 gene expression percentage of Experiment group B, Experiment group E and Experiment group J was decreased to 10% or lower as compared with the MMP2 gene expression percentage of Control group (expression of the control group was regarded as 100%). In other words, the MMP2 gene expression inhibition in Experiment group B, Experiment group E and Experiment group J reached 90% or above. In addition, as compared with that of Control group, the MMP2 gene expression percentage of Experiment group C was decreased to about 40% (expression of Control group was regarded as 100%). In other words, Experiment group C inhibited the MMP2 gene expression for about 60%. Therefore, when the peptide includes SEQ ID NO: 2, SEQ ID NO: 3, SEQ ID NO: 5 and SEQ ID NO: 10 or a combination thereof, it can be used for inhibiting the expression of the MMP2 gene, and preventing the loss of skin collagen.

4 types of amino acid sequences as set forth in SEQ ID NO: 2, SEQ ID NO: 3, SEQ ID NO: 5 and SEQ ID NO: 10 all have the capability of inhibiting the MMP2 gene expression, so that a composition prepared from at least one amino acid sequence therein can also be used for inhibiting the MMP2 gene expression. In addition, the composition can be used for decreasing loss of skin collagen, reducing loss of skin moisture, reducing wrinkles or achieving a combination of these effects.

Then, the composition experiment groups (i.e., Experiment L, represented by the experiment group in the drawing) and the control group were subjected to gene expression analysis of COL4A1 gene (GeneID: 1282), HAS2 gene (GeneID: 3037), TIMP1 gene (GeneID: 7076), ELN gene (GeneID: 2006) and LOX gene (GeneID: 4015), as shown in FIG. 5 to FIG. 8.

(VII) Expression Analysis of COL4A1 Gene in Composition Experiment Group and Control Group COL4A1 gene is a gene of type IV collagen alpha 1 chain. Therefore, the increase of gene expression of the COL4A1 gene represents the increase in content of type IV collagen. The content of collagen in the skin can be increased.

Figure 5:
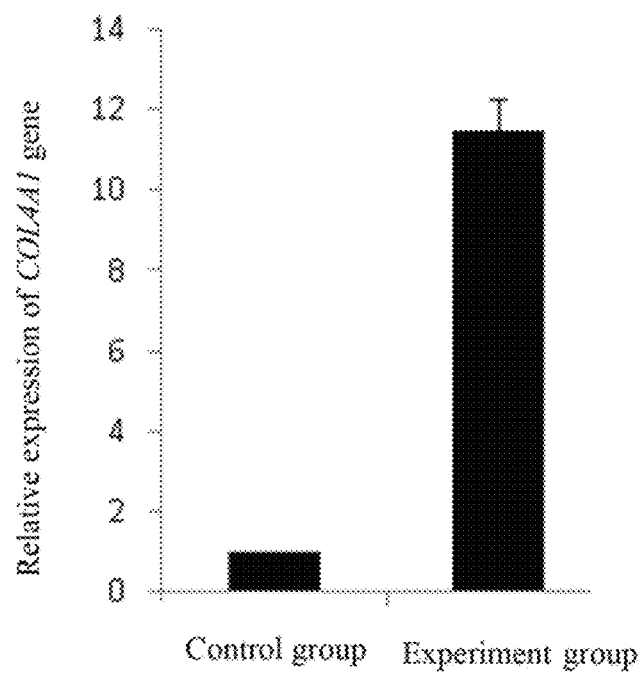
FIG. 5 is a bar chart showing relative expressions of COL4A1 gene in Experiment group and Control group in accordance with some embodiments of the present invention.

Referring to FIG. 5, the COL4A1 gene expression of Experiment group L and Control group was tested by COL4A1-F (SEQ ID NO: 20) and COL4A1-R (SEQ ID NO: 21) primers. The results showed that the gene expression of Experiment group L was significantly upregulated as compared with the gene expression of Control group. For example, the COL4A1 gene expression level in Experiment group L was 11 folds of the COL4A1 gene expression level in Control group. Therefore, the composition can promote the COL4A1 gene expression, and can be used for promoting generation of skin collagen, improving density of skin collagen, and improving skin elasticity. Therefore, the composition can be used for reducing wrinkles.

(VIII) Expression Analysis of HAS2 Gene in Composition Experiment Group and Control Group HAS2 gene is a gene of hyaluronan synthase 2 (HAS2). By observing the HAS2 gene expression, the HAS2 protein expression can be analyzed. When the HAS2 gene expression is increased, the amount of RNA transcribed from the HAS2 gene is increased, and it also represents that the content of protein translated from the RNA is increased. The HAS2 protein may be used for synthesizing hyaluronan, improving moisture content of the skin, maintaining skin cell structure, and reducing wrinkles.

Figure 6:
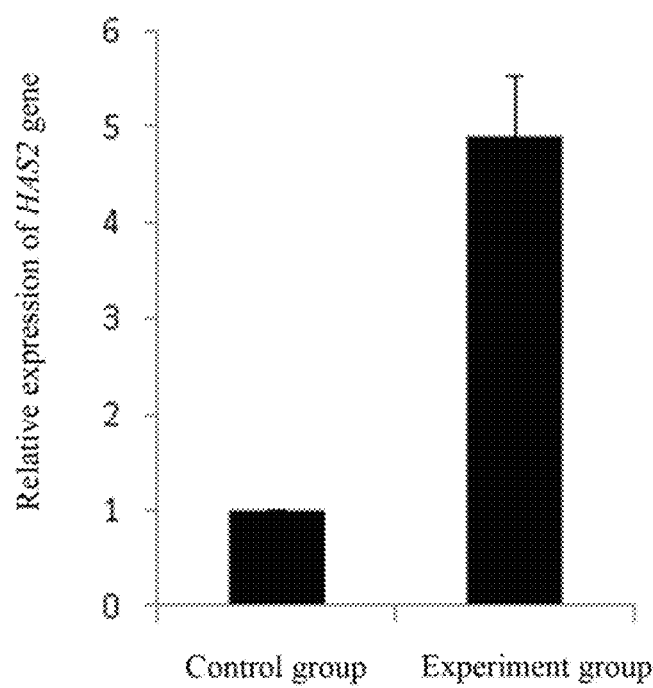
FIG. 6 is a bar chart showing relative expressions of HAS2 gene in Experiment group and Control group in accordance with some embodiments of the present invention.

Referring to FIG. 6, the HAS2 gene expression of Experiment group L and Control group was tested by HAS2-F (SEQ ID NO: 22) and HAS2-R (SEQ ID NO: 23) primers. The results showed that the gene expression of Experiment group L was significantly upregulated as compared with the gene expression of Control group. For example, the HAS2 gene expression level in Experiment group L was 5 folds of the HAS2 gene expression level in Control group. Therefore, the composition can promote the HAS2 gene expression, and can be used for improving skin moisture. Therefore, the composition can be used for reducing wrinkles.

Figure 7:
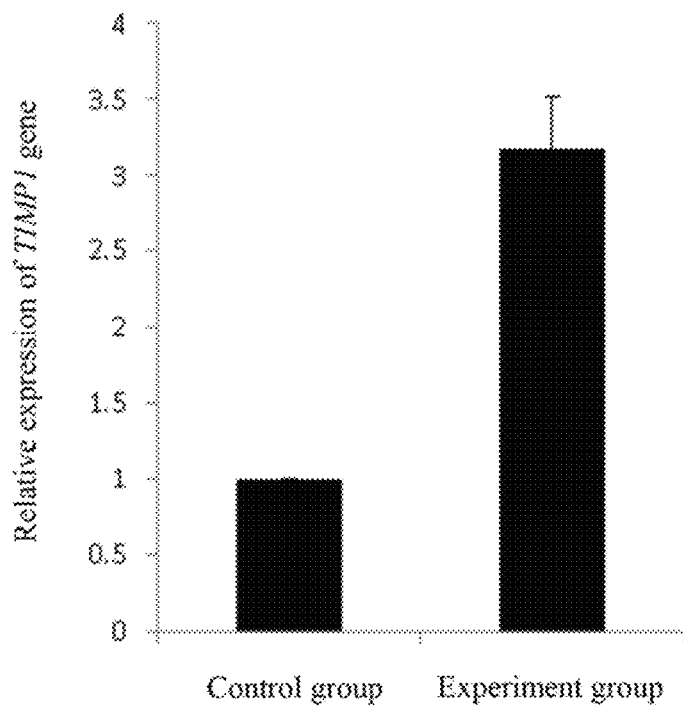
FIG. 7 is a bar chart showing relative expressions of TIMP1 gene in Experiment group and Control group in accordance with some embodiments of the present invention.

(IX) Expression Analysis of TIMP1 Gene in Composition Experiment Group and Control Group Referring to FIG. 7, the TIMP1 gene expression of Experiment group L and Control group was tested by TIMP1-F (SEQ ID NO: 16) and TIMP1-R (SEQ ID NO: 17) primers. The results showed that the gene expression of Experiment group L was significantly upregulated as compared with the gene expression of Control group. For example, the TIMP1 gene expression level in Experiment group L was 3 folds of the TIMP1 gene expression level in Control group. Therefore, the composition can promote the TIMP1 gene expression, and can be used for preventing loss of skin collagen. Therefore, the composition can be used for reducing wrinkles.

(X) Expression Analysis of ELN Gene and LOX Gene in Composition Experiment Group and Control Group ELN gene is a gene of elastin (ELN). LOX gene is a gene of lysyl oxidase (LOX). The elastin (ELN) can be combined with the elastic protein. The LOX protein can be combined with collagen and elastic fiber. Therefore, by observing the ELN gene and LOX gene expression, the expression level of the ELN protein and the LOX protein in the skin can be observed. The conditions of promoting the contents of the ELN protein and the LOX protein are both beneficial to skin elasticity improvement.

Figure 8:
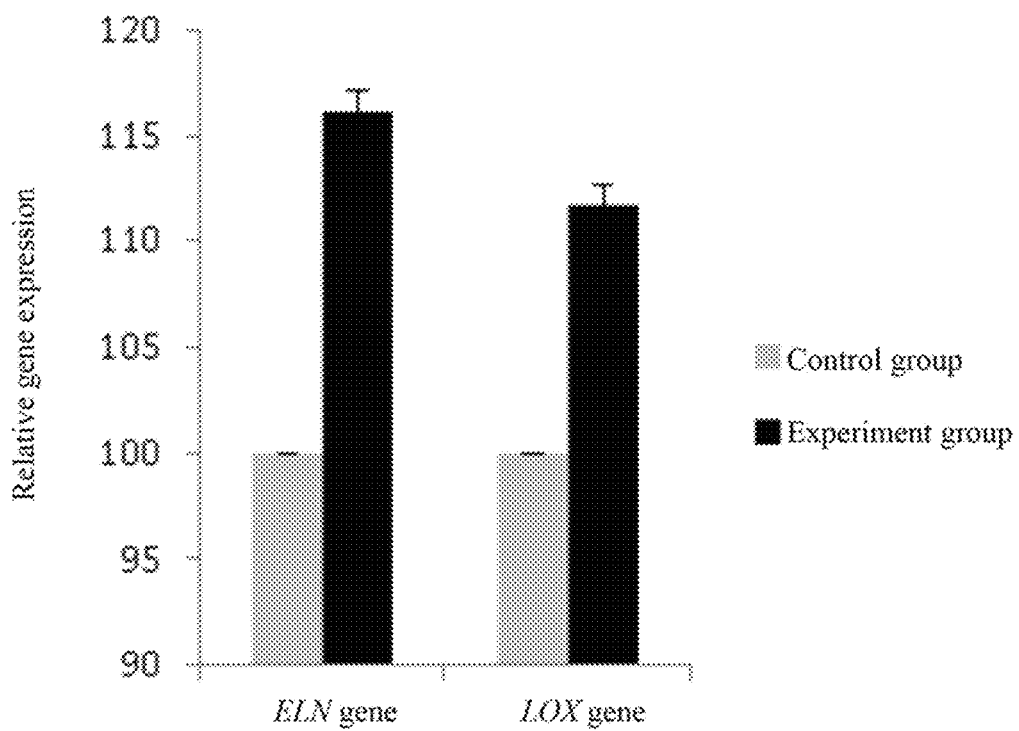
FIG. 8 is a bar chart showing relative expressions of ELN gene and LOX gene in Experiment group and Control group in accordance with some embodiments of the present invention.

Referring to FIG. 8, the ELN gene expression in Experiment group L and Control group was tested by ELN-F (SEQ ID NO: 24) and ELN-R (SEQ ID NO: 25) primers, and the LOX gene expression of Experiment group L and Control group was tested by LOX-F (SEQ ID NO: 14) and LOX-R (SEQ ID NO: 15) primers. The results showed that the expression of ELN gene and LOX gene in Experiment group L was respectively upregulated as compared with those of Control group. For example, when the ELN gene expression level in Control group was 100%, the ELN gene expression level in Experiment group L was 116%. When the LOX gene expression level in Control group was 100%, the LOX gene expression level in Experiment group L was 112%. Therefore, the composition can promote the expression of ELN gene and LOX gene, and can be used for promoting generation of collagen, improving density of skin collagen, improving skin elasticity, reducing wrinkles or achieving a combination of these effects.

In order to confirm the effect of the composition on the human skin, the composition was prepared from the peptide including 11 types of amino acid sequences (i.e., SEQ ID NO: 1 to SEQ ID NO: 11). In addition, the composition used in experiments below for testing the human body effects was tilapia fish skin collagen peptide powder (purchased from LAPI, Italy) including 11 types of amino acid sequences (i.e., SEQ ID NO: 1 to SEQ ID NO: 11) as identified in Example I and Example II.

(XI) Experiment Group and Experiment Design

Subjects were asked to take the composition or commercially available fish collagen every day. After 4 weeks of consumption, skin conditions (wrinkles, moisture loss, skin elasticity and collagen density) of the subjects were observed by instruments (VISIA Complexion Analysis (Canfield Scientific, Inc., USA) and DermaLab® Combo collagen probe instrument), and the effect of the composition or the commercially available fish collagen on the skin was observed.

Among 15 subjects, the Experiment group (8 persons) was asked to take the composition and the Control group (7 persons) was asked to take the commercially available fish collagen. In addition, the subjects needed to take 3 g of composition or commercially available fish collagen every day for 4 consecutive weeks. In addition, it should be noted that the "commercially available fish collagen" was not prepared from tilapia skin.

(XII) In Vivo Effects

Test results were obtained by comparing values at the $0^{th}$ week and 4th week altogether. The values at the $0^{th}$ week were measured before the test, and represented the skin conditions of all subjects without consuming of the composition or the commercially available fish collagen. The values measured at the $0^{th}$ week were regarded as 100%. The values at the $4^{th}$ week were measured after consumption for four consecutive weeks. It should be noted that the skin conditions depicted in the drawings were shown by relative percentages. Standard deviations were calculated by an STDEV formula of Excel software, and statistically significant differences were analyzed by one-tailed student t-test in the Excel software. In the drawings, "*" represents $p<0.05$, "" represents p<0.01, and "*" represents p<0.001. When p<0.05, it represents that there are statistical differences.

Figure 9:
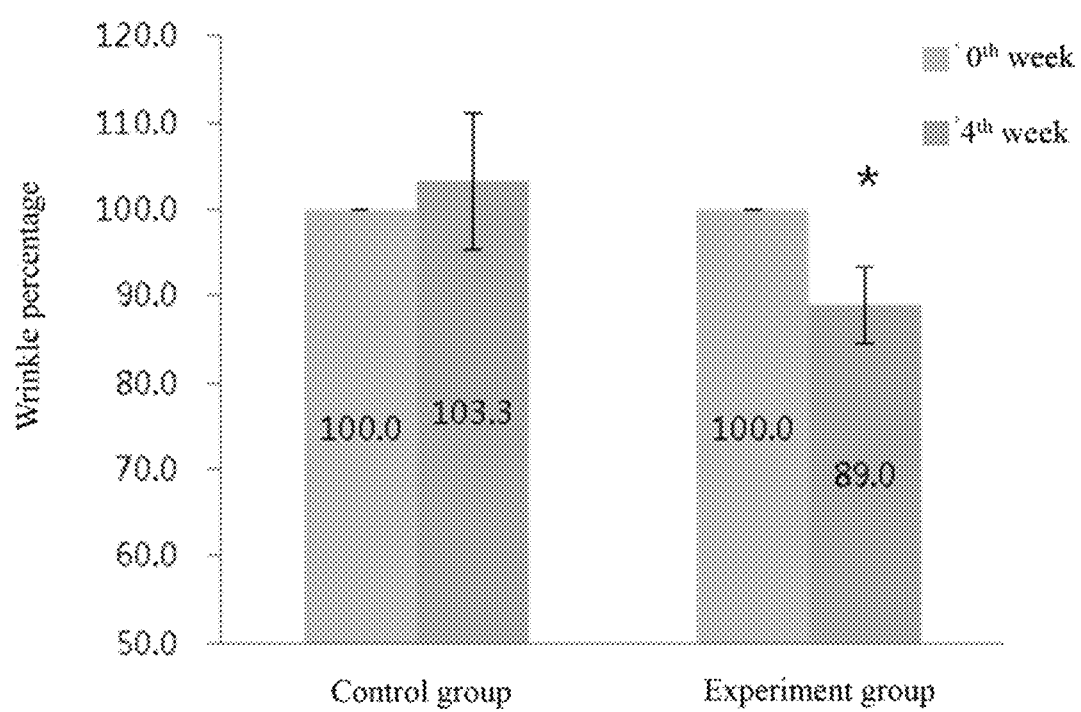
FIG. 9 is a bar chart showing wrinkle percentages of Experiment group and Control group at the $0^{th}$ week and $4^{th}$ week in accordance with some embodiments of the present invention.
Figure 10:
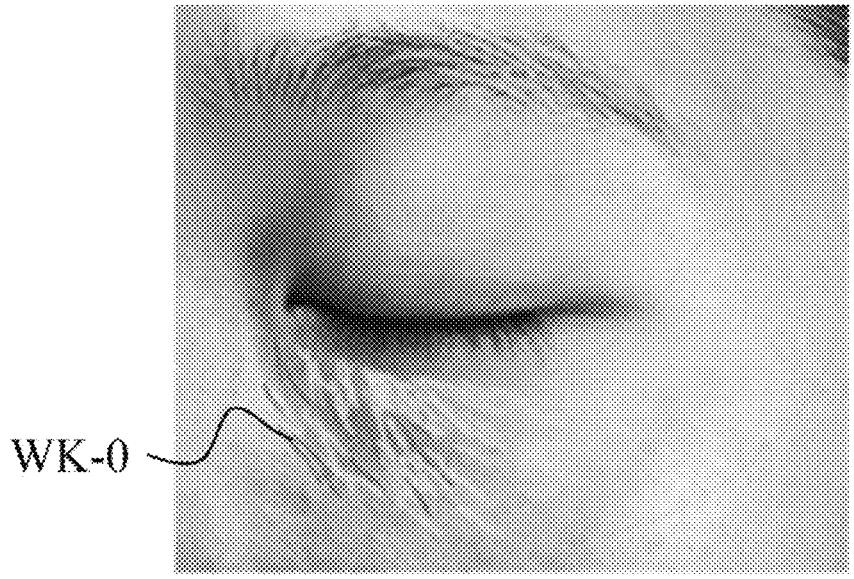
FIG. 10 is a photo of skin wrinkles of Experiment group at the $0^{th}$ week in accordance with some embodiments of the present invention.
Figure 11:
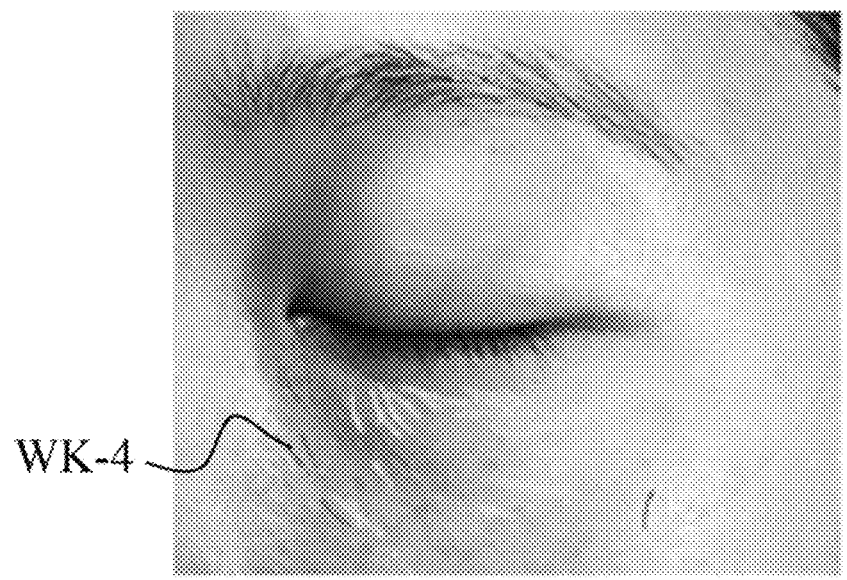
FIG. 11 is a photo of skin wrinkles of Experiment group at the $4^{th}$ week in accordance with some embodiments of the present invention.

Referring to FIG. 9, the results showed that the wrinkles of Control group were not reduced after consumption of the commercially available fish collagen for 4 consecutive weeks. The wrinkles of Experiment group were significantly reduced by 11% (were 89%) after continuous consumption of the composition as compared with those at the $0^{th}$ week. Then, referring to FIG. 10 and FIG. 11, the wrinkles WK-0 under the eyes of the subject of Experiment group were many and densely distributed at the $0^{th}$ week, as shown in FIG. 10. The wrinkles WK-4 under the eyes of the subject of Experiment group were reduced and sparsely distributed at the $4^{th}$ week, as shown in FIG. 11. Therefore, as compared with Control group, Experiment group demonstrated that the wrinkles could be effectively reduced (for example, the wrinkles were reduced) by taking the composition as in Experiment group.

Figure 12:
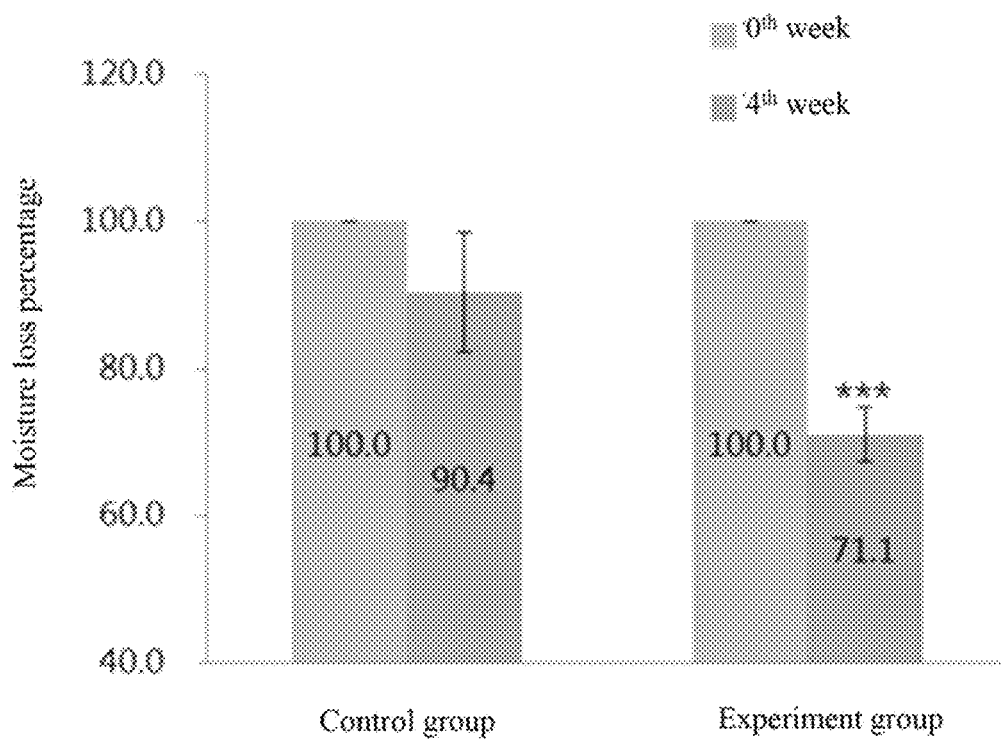
FIG. 12 is a bar chart showing moisture loss percentages of Experiment group and Control group at the $0^{th}$ week and $4^{th}$ week in accordance with some embodiments of the present invention.
Figure 13:
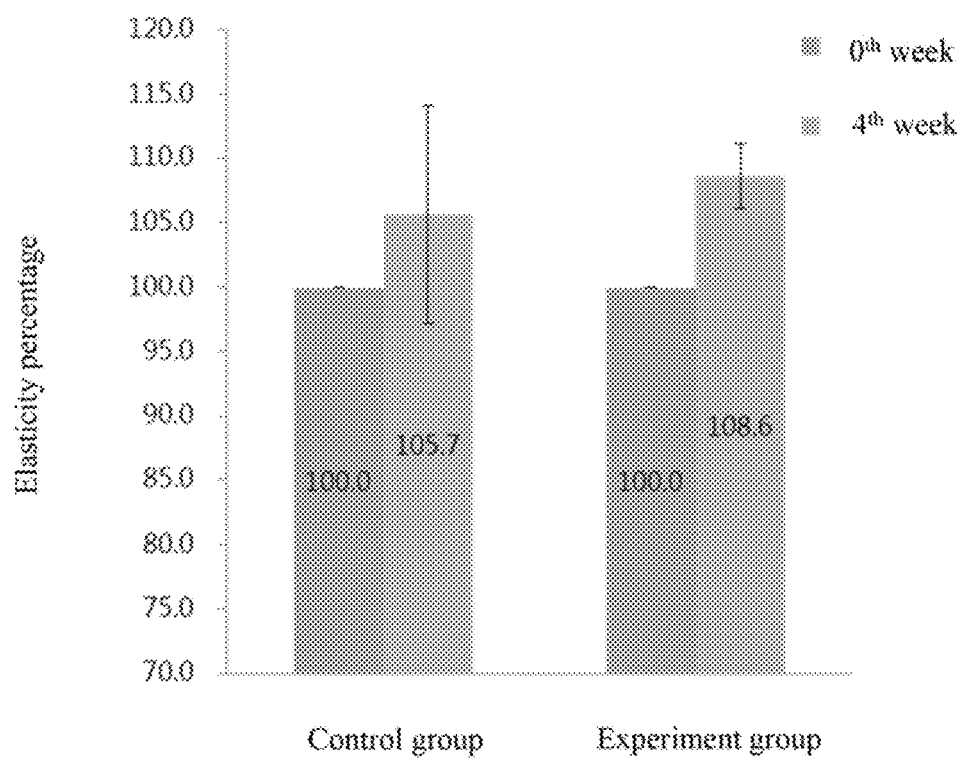
FIG. 13 is a bar chart showing elasticity percentages of Experiment group and Control group at the $0^{th}$ week and $4^{th}$ week in accordance with some embodiments of the present invention.
Figure 14:
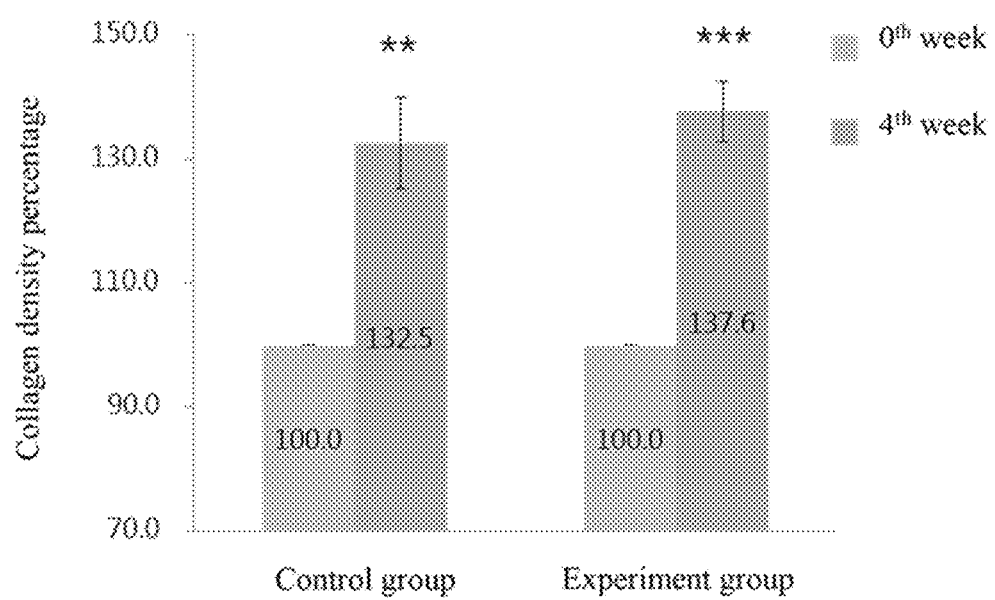
FIG. 14 is a bar chart showing collagen density percentages of Experiment group and Control group at the $0^{th}$ week and $4^{th}$ week in accordance with some embodiments of the present invention.
Figure 15:
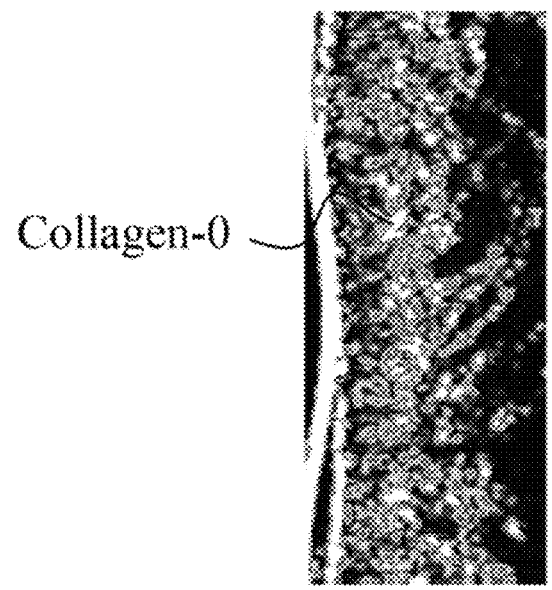
FIG. 15 is a diagram showing a collagen density analysis of Experiment group at the $0^{th}$ week in some embodiments of the present invention.
Figure 16:
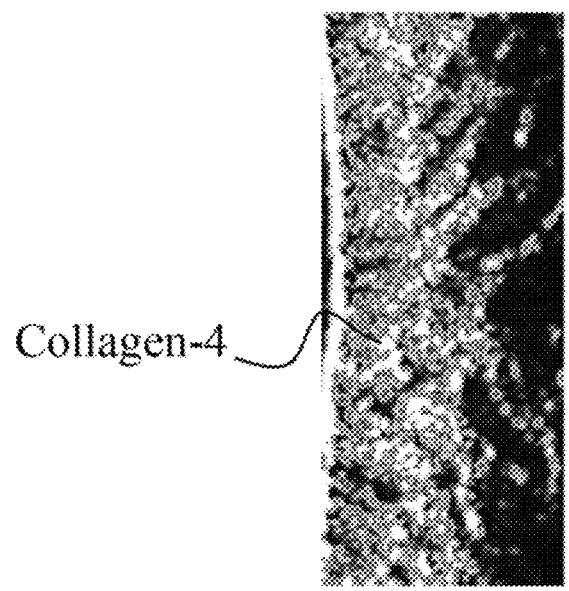
FIG. 16 is a diagram showing a collagen density analysis of Experiment group at the $4^{th}$ week in some embodiments of the present invention.

In addition, the values of Experiment group and Control group, such as percentage of moisture loss (as shown in FIG. 12), percentage of skin elasticity (as shown in FIG. 13) and skin collagen density (as shown in FIG. 14 to FIG. 16) were compared.

Referring to FIG. 12, by comparing moisture loss of Experiment group at the $0^{th}$ week and the $4^{th}$ week, the value was shown to decrease from 100% to 71.7%, which represented that skin moisture of the 8 subjects were improved by 28.9%. On the other hand, when comparing moisture loss of Control group at the $0^{th}$ week and the $4^{th}$ week, it was observed that the value was decreased from 100% to 90.4%, which represented that skin moisture of the 7 subjects were not significantly improved.

Referring to FIG. 13, by comparing skin elasticity of Experiment group at the $0^{th}$ week and the $4^{th}$ week, it could be observed that the value at the $4^{th}$ week was improved by 8.6% as compared with that at the $0^{th}$ week, which represented that skin elasticity of the 8 subjects was improved. In addition, when comparing skin elasticity of Control group at the $0^{th}$ week and the $4^{th}$ week, it was observed that the value at the $4^{th}$ week was improved by 5.7% as compared with that at the $0^{th}$ week. In other words, the effect of the composition for improving skin elasticity was better than that of the commercially available fish collagen.

Referring to FIG. 14 to FIG. 16, by comparing the density of skin collagen of Experiment group and Control group at the $0^{th}$ week and the $4^{th}$ week, it could be observed that the value of Experiment group at the week was improved by 37.6% s compared with that at the $0^{th}$ week, the value of Control group at the $4^{th}$ week was improved by 32.5% as compared with that at the $0^{th}$ week, which represented that the effect of the composition for improving the density of skin collagen was stronger than that of the commercially available fish collagen. Then, referring to FIG. 15 and FIG. 16, collagen density is represented by color brightness; specifically, white represent areas having the highest collagen density, whereas black represent areas having the lowest collagen density. At the $0^{th}$ week, the color areas representing the detected skin collagen density Collagen-0 of the subjects in Experiment group were generally white and the distribution of the white areas were sparse, as shown in FIG. 15. At the $4^{th}$ week, the white areas for representing the detected skin collagen density Collagen-4 of the subjects in Experiment group were generally increased, and were densely distributed, as shown in FIG. 16. Therefore, as compared with Control group, Experiment group taking the composition has the advantage that the collagen density of the subjects was effectively improved.

Therefore, the composition was prepared from the peptides including at least one amino acid sequence as set forth in SEQ ID NO: 1 to SEQ ID NO: 11. The composition at least had the capability of regulating the expression of at least one gene of FBN1 gene, LOX gene, TIMP1 gene and MMP2 gene. In addition, when the composition is prepared from the peptides including 11 types of peptides (the amino acid sequences are respectively SEQ ID NO: 1 to SEQ ID NO: 11), the composition had the capability of regulating the expression of at least one gene of COL4A1 gene, HAS2 gene, TIMP1 gene, ELN gene and LOX gene. In addition, the composition prepared from the peptide having at least one amino acid sequence as set forth in SEQ ID NO: 1 to SEQ ID NO: 11 could have at least one of the following effects: promoting generation of skin collagen, improving density of skin collagen, preventing loss of skin collagen, reducing loss of skin moisture, improving skin elasticity, and reducing wrinkles.

Based on the above, the peptide as the bioactive compound according to any embodiment of the present invention can be used for preparing the composition for improving skin conditions. In addition, the peptide includes at least one amino acid sequence as set forth in SEQ ID NO: 1 to SEQ ID NO: 11. In some embodiments, the peptide can regulate the expression of at least one gene of FBN1 gene, LOX gene, TIMP1 gene and MMP2 gene. In addition, the composition prepared from the peptide is also the composition capable of regulating the expression of at least one gene of FBN1 gene, LOX gene, TIMP1 gene and MMP2 gene. In some embodiments, the composition may be used for regulating the expression of COL4A 1 gene, HAS2 gene and ELN gene. In some embodiments, the composition can be used for promoting generation of skin collagen, improving density of skin collagen, preventing loss of skin collagen, reducing loss of skin moisture, improving skin elasticity, reducing wrinkles or achieving a combination of these effects.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for improving a skin condition of a subject in need thereof comprising administering to the subject a composition comprising a bioactive compound, wherein the bioactive compound is a peptide, the peptide comprises at least one full-length sequence selected from the group consisting of SEQ ID NO: 1 to SEQ ID NO: 11, each of the full-length sequence is a peptide of fish skin; and the improvement of skin condition comprises reducing wrinkles.

2. The method according to claim 1, wherein the improvement of skin condition further comorises promoting generation and improving density of skin collagen; the peptide is capable of regulating at least one gene of human fibroblast fibrillin-1 (FBN1) and type IV collagen alpha 1 chain (COL4A1); and the peptide for regulating FBN1 comprises at least one full-length sequence selected from the group consisting of SEQ ID NO: 2 to SEQ ID NO: 11.

3. The method according to claim 1, wherein the improvement of skin condition further comprises preventing loss of skin collagen; wherein the peptide is capable of regulating at least one gene of tissue inhibitor of metalloproteinases 1 (TIMP1) and matrix metalloproteinase-2 (MMP2); the peptide for regulating TIMP1 comprises at least one full-length sequence selected from the group consisting of SEQ ID NO: 2, SEQ ID NO: 6, SEQ ID NO: 8, SEQ ID NO: 9 and SEQ ID NO: 11; and the peptide for regulating MMP2 comprises at least one full-length sequence selected from the group consisting of SEQ ID NO: 2, SEQ ID NO: 3, SEQ ID NO: 5 and SEQ ID NO: 10.

4. The method according to claim 1, wherein the improvement of skin condition further comprises reducing loss of skin moisture; and the peptide is capable of regulating an hyaluronan synthase 2 (HAS2) gene.

5. The method according to claim 1, wherein the improvement of skin condition further comprises improving skin elasticity; the peptide is capable of regulating at least one gene of FBN1, lysyl oxidase (LOX) and elastin (ELN); and the peptide for regulating LOX comprises at least one full-length sequence selected from the group consisting of SEQ ID NO: 2, SEQ ID NO: 5, SEQ ID NO: 9 and SEQ ID NO: 11.

6. The method according to claim 1, wherein the fish skin is a tilapia skin.

7. The method according to claim 1, wherein a source of the peptide of the fish skin comprises fish skin cells, fish skin collagen or fish muscle cells.

\* \* \* \* \*